(12) United States Patent
Fiegler

(10) Patent No.: US 9,594,013 B2
(45) Date of Patent: Mar. 14, 2017

(54) FOREIGN BODY INSPECTION IN FILLED CONTAINERS

(71) Applicant: KRONES AG, Neutraubling (DE)

(72) Inventor: Rudolf Fiegler, Neutraubling (DE)

(73) Assignee: KRONES AG, Neutraubling (DE)

( * ) Notice: Subject to any disclaimer, the term of this patent is extended or adjusted under 35 U.S.C. 154(b) by 300 days.

(21) Appl. No.: 14/169,198

(22) Filed: Jan. 31, 2014

(65) Prior Publication Data

US 2014/0216142 A1 Aug. 7, 2014

(30) Foreign Application Priority Data

Feb. 5, 2013 (DE) .................. 10 2013 201 798

(51) Int. Cl.
*G01M 7/00* (2006.01)
*G01N 19/08* (2006.01)
(Continued)

(52) U.S. Cl.
CPC .............. *G01N 19/08* (2013.01); *G01M 7/00* (2013.01); *G01M 7/025* (2013.01); *G01M 7/027* (2013.01);
(Continued)

(58) Field of Classification Search
CPC .... F02D 41/403; F02M 45/063; G01M 7/025; G01M 7/027; G01M 7/04;
(Continued)

(56) References Cited

U.S. PATENT DOCUMENTS 5,755,074 A * 5/1998 Fetters ...................... B07C 5/02
198/395
5,893,700 A * 4/1999 Kronseder .............. B08B 9/426
198/803.9
(Continued)

FOREIGN PATENT DOCUMENTS

CN 1435679 A 8/2003
DE 102004051961 A1 5/2006
(Continued)

OTHER PUBLICATIONS

Search report for DE 10 2013 201 798.7, dated Jul. 7, 2013.
(Continued)

*Primary Examiner* — David A Rogers
*Assistant Examiner* — Gedeon M Kidanu
(74) *Attorney, Agent, or Firm* — Marshall, Gerstein & Borun LLP

(57) ABSTRACT

An apparatus for inspecting filled containers for foreign bodies that may be contained therein, where the filled container is mechanically excited by vibration or rotation so as to cause the possibly existing foreign bodies to rotate. The acoustic signals produced by the foreign bodies impacting on the inner wall of the container are detected and analyzed. Any signal detection is separated from mechanical excitation, and mechanical excitation is separated from container transport in that the signal-detecting sensor is applied to the container only after the end of the mechanical excitation. The mechanical excitation is executed by an excitation element that is brought into contact with the container independently of the holding elements used for the purpose of transport.

18 Claims, 3 Drawing Sheets

(51) Int. Cl.
*G01M 11/08* (2006.01)
*G01N 29/14* (2006.01)
*G01N 29/46* (2006.01)
*G01M 7/02* (2006.01)
*G01M 7/04* (2006.01)
*G01N 21/90* (2006.01)

(52) U.S. Cl.
CPC ............ *G01M 7/04* (2013.01); *G01M 11/088* (2013.01); *G01N 29/14* (2013.01); *G01N 29/46* (2013.01); *G01N 21/9027* (2013.01); *G01N 2291/2695* (2013.01)

(58) Field of Classification Search
CPC ............... G01N 19/08; G01N 21/9027; G01N 2291/2695; G01N 29/14; G01N 29/46; H04L 1/0036; H04L 25/0224; H04L 27/16; H04L 27/2655
USPC ........................................................ 73/61.75
See application file for complete search history.

(56) References Cited

U.S. PATENT DOCUMENTS

| | | | |
|---|---|---|---|
| 6,289,724 B1* | 9/2001 | Varma | G01M 7/00 73/12.01 |
| 6,851,313 B2* | 2/2005 | Fehrenbach | G01F 23/2967 73/290 R |
| 7,295,317 B2* | 11/2007 | Niedermeier | G01N 21/9027 250/223 B |
| 7,743,907 B2* | 6/2010 | Weinbrenner | B67C 3/22 141/144 |
| 8,576,279 B2 | 11/2013 | Fiegler | |
| 2007/0039390 A1* | 2/2007 | Duncan | G01N 29/226 73/606 |
| 2010/0315254 A1* | 12/2010 | Morand | B65G 43/08 340/689 |
| 2011/0025840 A1* | 2/2011 | Fiegler | G01N 21/9027 348/127 |
| 2012/0113248 A1* | 5/2012 | Fiegler | G01N 21/90 348/125 |
| 2012/0201576 A1* | 8/2012 | Uno | G03G 15/0813 399/281 |
| 2013/0146207 A1* | 6/2013 | Herrmann | B65C 9/40 156/64 |
| 2013/0233437 A1* | 9/2013 | Herrmann | B67C 3/007 141/1 |
| 2013/0248321 A1* | 9/2013 | Herrmann | G01N 29/046 198/339.1 |

FOREIGN PATENT DOCUMENTS

| | | |
|---|---|---|
| DE | 102010018823 A1 | 11/2011 |
| DE | 102010053771 A1 | 6/2012 |
| DE | 102010053772 A1 | 6/2012 |
| EP | 0726216 B1 | 9/1998 |
| EP | 0795500 B1 | 11/2002 |
| WO | WO-2004053471 A1 | 6/2004 |
| WO | WO-2012076088 A1 | 6/2012 |

OTHER PUBLICATIONS

The Second Office Action for Application No. 201410045236.7, dated Aug. 1, 2016.
The First Office Action for Application No. 201410045236.7, dated Dec. 3, 2015.

* cited by examiner

FOREIGN BODY INSPECTION IN FILLED CONTAINERS

CROSS-REFERENCE TO RELATED APPLICATION

The present application claims the benefit of priority of German Application No. 10 2013 201 798.7, filed Feb. 5, 2013. The priority application is incorporated herein by reference in its entirety.

FIELD OF THE DISCLOSURE

The present disclosure relates to an apparatus and a method for inspecting filled containers for foreign bodies that may be contained therein.

BACKGROUND

When filling beverages or other liquids into containers, such as glass or plastic containers, it may be necessary to inspect the filled and closed containers for foreign bodies. During the filling process, e.g. individual machine parts, such as nuts, screws or the like, may get into the containers. Such large foreign bodies are comparatively easy to detect.

Foreign bodies that are difficult to detect are fine particles such as transparent glass fragments. Since containers often have scuffs or scratches on their bottom, it is often impossible to unequivocally identify glass fragments in comparison therewith.

For detecting such foreign bodies, WO 2004/053471 discloses a device for inspecting filled and closed receptacles. This publication discloses that the containers are caused to rotate, so that also the content of the container, including the glass fragments, will rotate. After the container has been brought to a stop, the liquid including the glass fragments will continue to rotate, so that the fragments can easily be detected by respective camera recordings.

Causing the content of a container to move through rotation of the container necessitates a comparatively large expenditure of time, so that high target throughput rates will here lead to a comparatively high investment in machinery.

DE 10 2004 051961 A1 discloses an apparatus for inspecting a filled container for foreign bodies. In the case of this apparatus the filled and closed container can be held in a movable holding device and moved continuously on a circulation path, preferably together with an inspection camera which is adapted to be moved along with the holding device. Making use of a vibration unit for producing vibrations in the container, foreign bodies, such as fine glass fragments, on the bottom of the container are caused to move and can thus be recorded with the inspection camera.

A disadvantage of this apparatus is the technical outlay entailed by image processing as well as the limitation to transparent containers and liquids.

Also DE 10 2010 053 771 A1 discloses an apparatus for inspecting a filled container for foreign bodies. In this apparatus the containers are mechanically excited via the holding device, so that the liquid contained therein, including foreign bodies that may be contained in the liquid, moves relative to the container wall. The signals that may result from impacts of foreign bodies on the housing wall are detected by a piezosensor integrated in the holding device. The signals provided by the piezosensor are transmitted to an analysis unit by means of a slip ring or by wireless transmission.

However, the integration of the piezosensors in the holding device, which must also be configured for mechanical excitation, requires a substantial constructional outlay that is opposed to a reasonably-priced solution.

SUMMARY OF THE DISCLOSURE

It is therefore one aspect of the present disclosure to improve the apparatus and the method for inspecting a container for foreign bodies.

It is another aspect of the present disclosure to decouple the mechanical excitation of the foreign bodies that may be contained in the containers, acoustic signal detection and container transport from one another.

According to a first aspect of the present disclosure, an apparatus is provided for inspecting filled containers for foreign bodies while the container to be inspected is fixed in a transport unit by means of a holding element and transported along a predetermined trajectory. The apparatus comprises an excitation device configured for mechanically exciting the container so that foreign bodies that may be present in the container will be caused to move, a sensor, and an application device configured for applying the sensor to the container, the sensor being configured for detecting, when applied, acoustic signals of the foreign bodies that have been caused to move through mechanical excitation. The application device is additionally configured for applying the sensor to the container only after the end of the mechanical excitation. Excitation and signal detection are thus decoupled, so that the sensors need not be moved together with the containers when the latter are mechanically excited.

Preferably, the application device is arranged downstream of the excitation device, when seen in the direction of transport, so that excitation and signal detection will take place in not too close proximity. The transport unit may especially comprise a processing carousel and a downstream transfer star wheel. The excitation device may be arranged in the processing carousel or in a transition area between the processing carousel and the transfer star wheel, and the application device may be arranged in the transfer star wheel.

According to a second aspect of the present disclosure, an apparatus is provided for inspecting filled containers for foreign bodies while the container to be inspected is fixed in a transport unit by means of a holding element and transported along a predetermined trajectory. The apparatus comprises an excitation device configured for mechanically exciting the container so that foreign bodies that may be present in the container will be caused to move, a sensor, and an application device configured for applying the sensor to the container, the sensor being configured for detecting, when applied, acoustic signals of the foreign bodies that have been caused to move through mechanical excitation. The excitation device is adapted to be brought into contact with the container independently of the holding element. Excitation and transport of the containers are thus decoupled, whereby the constructional outlay is substantially reduced.

The mechanical excitation of the foreign bodies that may perhaps be present can be executed in any suitable way. In particular, the excitation device may be configured for causing the container to rotate and/or vibrate so that the foreign bodies that may be present are caused to carry out a gyratory and/or bouncing movement.

According to a preferred embodiment, the excitation device comprises a vibration unit that can be preloaded relative to the container via an elastic element, preferably a spring. This kind of excitation device can be used for retrofitting even existing transport units without major constructional outlay being necessary. The excitation unit may, however, also comprise a motor that is capable of causing the container to rotate, preferably about its longitudinal axis.

The sensor may be brought into contact with the container at any suitable point of the latter. Preferably, however, an application device is provided, with the application device being configured for bringing the sensor into contact with an outer wall, preferably a side wall, of the container, since the outer side wall of the containers (in the case of bottles in particular in the area of the body of the bottle) is easily accessible in conventional transport units. The sensor, when applied, moves in a advantageous manner along or at least parallel to the trajectory predetermined by the transport unit—but not in a circular motion superimposed on the trajectory, as would be the case for the side walls of rotating containers.

Any sensor configured for detecting acoustic signals originating from foreign bodies impacting on an inner wall of the container may be used for signal detection, in particular sensors with piezoelectric elements. If desired, the sensor may be integrated in a clamp of a clamp star wheel of the transport unit, so that additional means for guaranteeing a mechanical contact between the sensor and the container will not be necessary.

For controlling the application movement of the sensor to the container, the application device may comprise any suitable means, such as a control cam, a lifting cam, a motor, a linear motor or a servomotor.

According to an advantageous embodiment, the apparatus further comprises an analysis unit configured for analyzing the acoustic signal detected by the sensor in the time and/or the frequency domain and for deciding, on the basis of the analysis, whether or not a foreign body is present in the container. An output signal of the analysis unit can then be used by the process control for discharging the containers in question.

In accordance with the first aspect of the present disclosure, the disclosure provides a method for inspecting filled containers for foreign bodies while the container to be inspected is fixed in a transport unit by means of a holding element and transported along a predetermined trajectory. The method comprises the steps of mechanically exciting a container so that foreign bodies that may be contained therein will be caused to move, applying a sensor to the container, and detecting, by means of the sensor applied, acoustic signals originating from the foreign bodies that have been caused to move through mechanical excitation. The method is characterized in that the sensor is applied to the container only after the end of the mechanical excitation.

In accordance with the second aspect of the present disclosure, the disclosure provides a method for inspecting filled containers for foreign bodies while the container to be inspected is fixed in a transport unit by means of a holding element and transported along a predetermined trajectory. The method comprises the steps of mechanically exciting a container by means of an excitation device so that foreign bodies that may be contained therein will be caused to move, applying a sensor to the container, and detecting, by means of the sensor applied, acoustic signals originating from the foreign bodies that have been caused to move through mechanical excitation. The method includes that the excitation device is brought into contact with the container independently of the holding element.

BRIEF DESCRIPTION OF THE DRAWINGS

The disclosure will be described in the following making reference to the figures enclosed, in which.

DETAILED DESCRIPTION OF THE PREFERRED EMBODIMENT

In an apparatus for inspecting filled containers for foreign bodies that may be contained therein, the filled container is mechanically excited by vibration or rotation, so as to cause the foreign bodies that may be contained therein to move. The acoustic signals resulting from foreign bodies impacting on the inner wall of the container are detected and evaluated. According to the present disclosure, the detection of these signals is separated from the mechanical excitation and the mechanical excitation is separated from the transport of the containers in that the signal-detecting sensor is applied to the container only after the end of the mechanical excitation and the mechanical excitation is executed by an excitation element, which is brought into contact with the container independently of the holding elements used for container transport.

Figure 1:
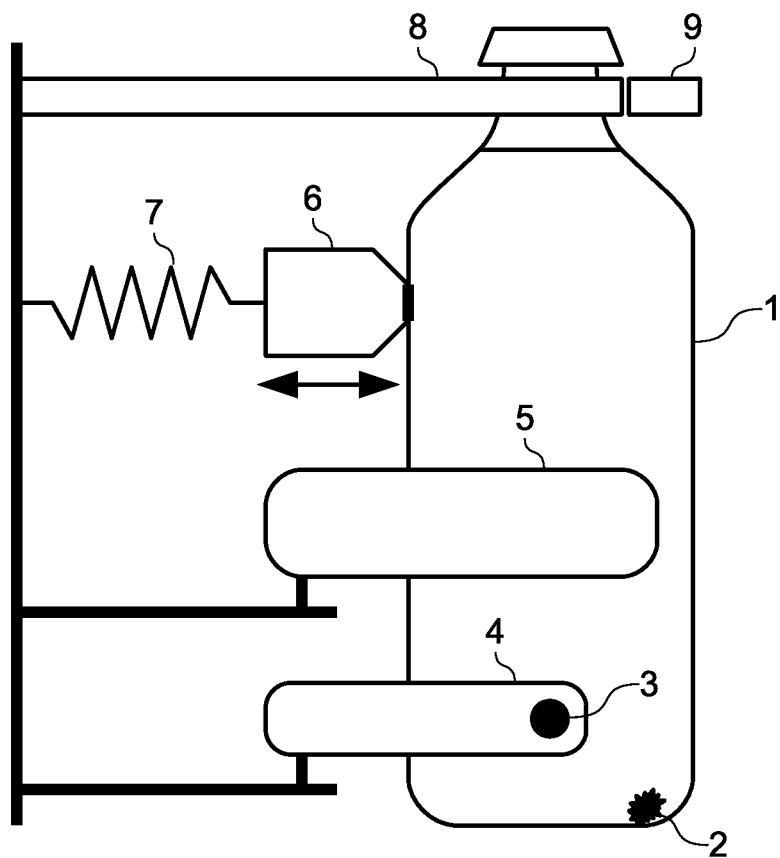
FIG. 1 shows a schematic view of the apparatus according to a first embodiment.

FIG. 1 shows a schematic view of the apparatus according to a first embodiment of the present disclosure. The container 1, e.g. a beverage bottle made of glass, plastic or the like, is held by clamps 5 of the type known e.g. from EP 0 726 216 B1 or EP 0 795 500 B1. The clamps themselves may be fixed to a carousel which is not shown in detail. The carousel may also have secured thereto a template 8 having recesses formed therein, in which the neck areas of the containers 11 are received and centered. The recesses can be closed by a circumferentially extending V-belt 9 on the radially outer side, so that the container necks are fixed in the template 8. Due to the template 8, the V-belt 9 and the clamps 5, the containers 1 are held at a predetermined position relative to the carousel. The containers 1 can be moved by means of the carousel on a predetermined horizontal circular path in a continuous circulatory movement.

Independently of the holding devices 5, a vibration unit 6 is arranged. This vibration unit may comprise a vibrator and a pusher. Both these elements can be elastically preloaded relative to the container 1 by means of a spring 7, so that the vibration unit 6 bears against the container wall with a certain pressure. The vibration unit 6 may be arranged above and/or below the clamps 5.

The vibration unit 6 may be configured for moving radially back and forth in the direction of the arrows. It is thus possible to grasp the container 1 first with the holding device 5, the template 8 and the V-belt 9 and to move the vibration unit 6 then into contact with the container 1. During this movement, preloading by means of the spring 7 will also take place. The travelling movement of the vibration unit 6 may be controlled by a control cam, in particular in the circulation area of an infeed star wheel and a discharge star wheel, where the containers 1 are introduced in the carousel and removed therefrom after one circulation.

It is also possible to configure the vibration unit 6 such that it is movable, so that the container 1 will be pressed against the vibration unit 6 and displace the latter against the force of the spring 7, when the container 1 is transferred to the position at which it can be held with the holding device 5. This means that, when the container 1 is introduced in the carousel, the vibration unit 6 will be displaced radially inwards and the spring 7 thus preloaded.

When the vibration unit 6 is in contact with the container 1, the container 1 can be mechanically excited by a vibration transmitted to the side wall of the container by the pusher of the vibration unit 6. Foreign bodies 2, such as glass fragments, can thus be caused to move.

Also a sensor 3 can be brought into contact with the container 1 by means of an application device 4, said sensor 3 being configured for detecting acoustic signals originating from the foreign bodies 2 that have been caused to move through mechanical excitation. The application device 4 may be configured as a gripper, which clasps around the container 1 and, in so doing, presses the sensor 3 against the container. The application device 4 may, however, also be configured as a single arm, which applies the sensor 3 laterally to the container 1. The application device 4 may also include an elastic element (not shown) preloading the sensor 3 relative to the container 1. The application device 4 may also be configured to move the sensor 3 similar to the vibration unit 6 in a radial direction and to press it against the container 1.

The sensor 3 may be brought into contact with the container 1 at any suitable point, in particular at the side wall or the bottom of the container. The sensor may, however, also be applied to the neck area or the closure of the container. According to a particularly preferred embodiment, the sensor 3 is integrated in the clamps 5 of the holding device. The sensor can thus be applied by means of the mechanism which is provided for controlling the clamps anyhow. A separate application device can be dispensed with.

The acoustic signal detected by the sensor can be analyzed in an analysis unit so as to detect the signal components which are characteristic of the presence of foreign bodies. The analysis can take place in the time and/or the frequency domain and can be carried out e.g. by a digital signal processor. For example, specific recurring frequency components that are characteristic of a bouncing movement of the foreign bodies can be detected. On the basis of the analysis result, it can be decided whether or not foreign bodies are present and the respective container can be isolated, if necessary.

The mechanical excitation of the container 1 through the vibration unit 6 and the detection of the signals by the sensor 3 need not necessarily take place at the same time. It may e.g. be of advantage to detect acoustic signals only after the end of the vibrational excitation so as to exclude interference signals, caused by the excitation itself, from the very beginning However, provided that the signals are adequately filtered, vibrational excitation and signal detection may also be executed simultaneously.

It may perhaps also be of advantage to apply the sensor 3 to the container only after the end of the mechanical excitation so as to avoid excessive mechanical loads on the sensor. Depending on the type of mechanical excitation, it will suffice to apply the sensor to the container immediately after the end of the mechanical excitation or within a few seconds after the end of the excitation, so that "post-clattering" of the foreign bodies can be detected.

Due to the separation of excitation and signal detection, signal detection need not take place at the same location or in the same part of the plant as the excitation. In particular, the detection device may be arranged downstream of the excitation device in the direction of transport. According to a preferred embodiment, the transition area between a processing carousel (e.g. a labeling carousel) and a subsequent transfer star wheel is configured as a vibration element which provides for mechanical excitation of the containers. The application of the sensors to the containers and the signal detection will they can only take place in the transfer star wheel.

The present disclosure is not limited to the clamps shown as holding elements in FIG. 1, but may be combined with any suitable holder for the containers, in particular with the centering elements and bottle tables described hereinbelow in connection with FIG. 2.

Nor is the present disclosure limited to a specific type of mechanical excitation. Instead of the above described vibrational excitations, also rotational excitations may be used, in the case of which the containers are caused to rotate e.g. about a vertical axis (if the containers are rotationally symmetrical, such as bottles, this will be the axis of rotational symmetry), so that also the liquid content of the containers, together with the foreign bodies that may be contained therein, is caused to rotate. After an abrupt stop of the rotational movement of the container, the content will continue to rotate and the foreign bodies will execute a gyratory movement and scratch along the inner wall of the container. The resultant acoustic signals can be detected by a sensor and analyzed.

Figure 2:
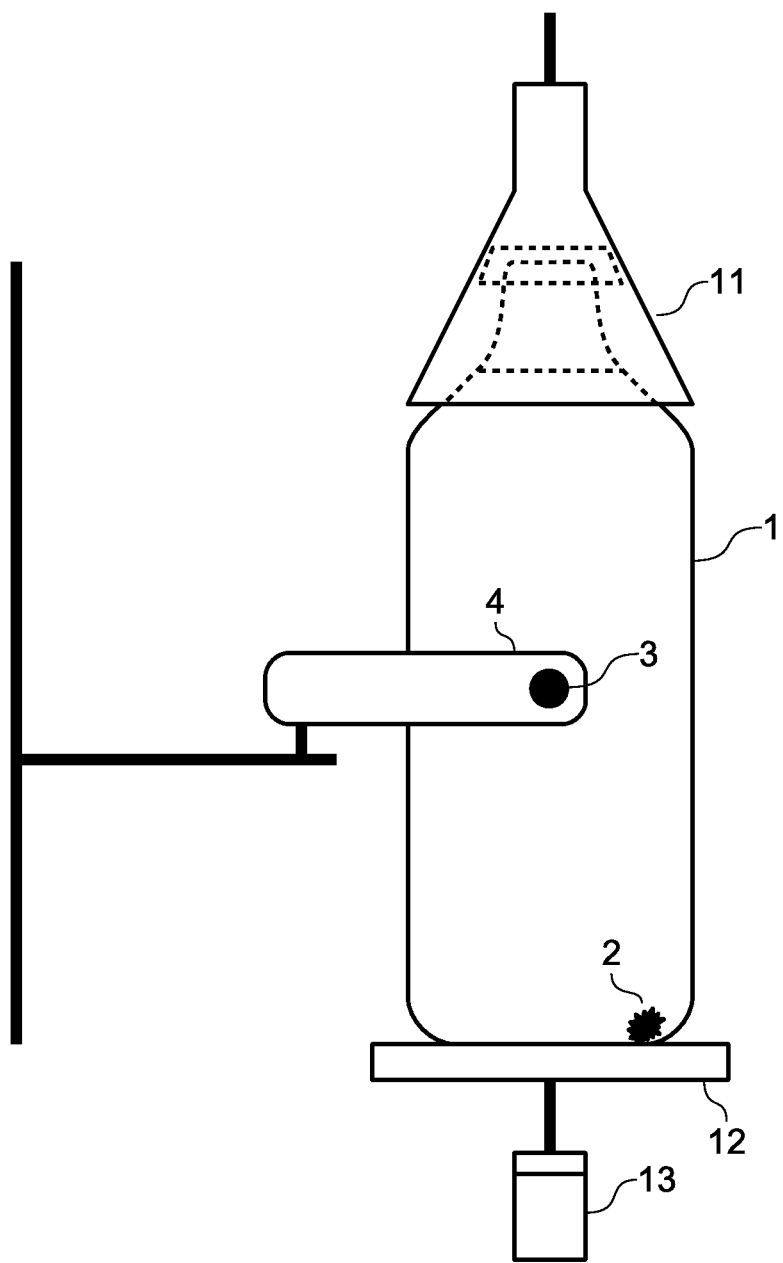
FIG. 2 shows a schematic view of the apparatus according to a second embodiment.

FIG. 2 shows a schematic view of the device according to a second embodiment of the present disclosure. The embodiment according to FIG. 2 differs from that shown in FIG. 1 with respect to the way of holding the container 1 and with respect to the type of mechanical excitation. As for the rest, this embodiment is similar to the embodiment according to FIG. 1. Identical reference numerals designate identical or similar elements.

The container 1, e.g. a beverage bottle made of glass, plastic or the like, is held by a conical centering element ("tulip") 11 and a bottle table 12. The holding elements 11, 12 may be part of a processing carousel, e.g. a labeling carousel. The holding elements 11, 12 may, however, also be part of an infeed or a discharge star wheel for such a processing carousel. As has been explained hereinbefore in connection with FIG. 1, the containers 1 can be held at a predetermined position relative to the carousel or the star wheel by the holding elements 11, 12 and moved by means of the carousel or the star wheel on a predetermined horizontal circular path in a continuous circulatory movement.

The centering element 11 and/or the bottle table 12 are configured for causing the container to rotate about a vertical axis (e.g. the axis of symmetry of the container). To this end, the centering element 11 and/or the bottle table 12 can be rotationally supported and coupled to a motor 13. In order to ensure a mechanical excitation of the foreign bodies that may perhaps be present in the container, the drive 13 of the centering element 11 and of the bottle table 12, respectively, is controlled such that the container will be caused to rotate until the content of the container has started rotating as well, before the rotation of the container is stopped.

After the end of excitation, i.e. when the rotation of the container has been stopped, a sensor 3 is applied to the container for detecting signals of the foreign bodies that may perhaps be present in the container. As has been explained hereinbefore in connection with FIG. 1, the application device 4, with which the sensor is applied to the container, may be configured as a gripper, which clasps around the container 1 and, in so doing, presses the sensor 3 against the container. The application device 4 may, however, also be configured as a single arm, which applies the sensor 3 laterally to the container 1. The application device 4 may also include an elastic element (not shown) preloading the sensor 3 relative to the container 1. In addition, the application device 4 may be configured to move the sensor 3 similar to the vibration unit 6 in FIG. 1 in a radial direction and to press it against the container 1. The sensor 3 may be brought into contact with the container 1 at any suitable point, in particular at the side wall of the container.

Due to the separation of excitation and signal detection, signal detection need not take place in the same part of the plant as the excitation. For example, when labeling has been finished, the containers may be caused to rotate versus the end of their transport in the labeling carousel, the detection being then executed only after transfer to a transfer star wheel. It goes without saying that the kind of holding elements holding the containers in the transfer star wheel may differ from those holding the containers in the labeling carousel. In particular, the above explained clamps 5, which are shown in FIG. 1, can be used in the transfer star wheel. In the transfer star wheel, the sensor 3 can be brought into contact with the container 1 at any suitable point. In the case of a clamp star wheel this may in particular also be the bottom of the container, the neck area or the closure of the container. According to a specially preferred embodiment, the sensor 3 is integrated in the clamps 5 of the holding device. The sensor can thus be applied by means of the mechanism which is provided for controlling the clamps anyhow. A separate application device can be dispensed with.

The embodiments described here can be combined in any suitable way. In particular, the vibrational excitation device shown in FIG. 1 may also be used in combination with the holding means in the form of centering elements and bottle tables shown in FIG. 2.

Due to the fact that the sensors are applied to the bottles only after the end of the excitation (when the rotation has been stopped), the sensors need not be rotated together with the containers, whereby possible problems concerning a transmission of signals between rotating sensors and the stationary analysis unit can be avoided. In addition, the sensors themselves are not subjected to mechanical excitation through rotation or vibration, whereby their durability and service life will be improved. If vibrational excitation is used, even existing labeling carousels having no servo bottle tables can be retrofitted with foreign body detection means.

Figure 3:
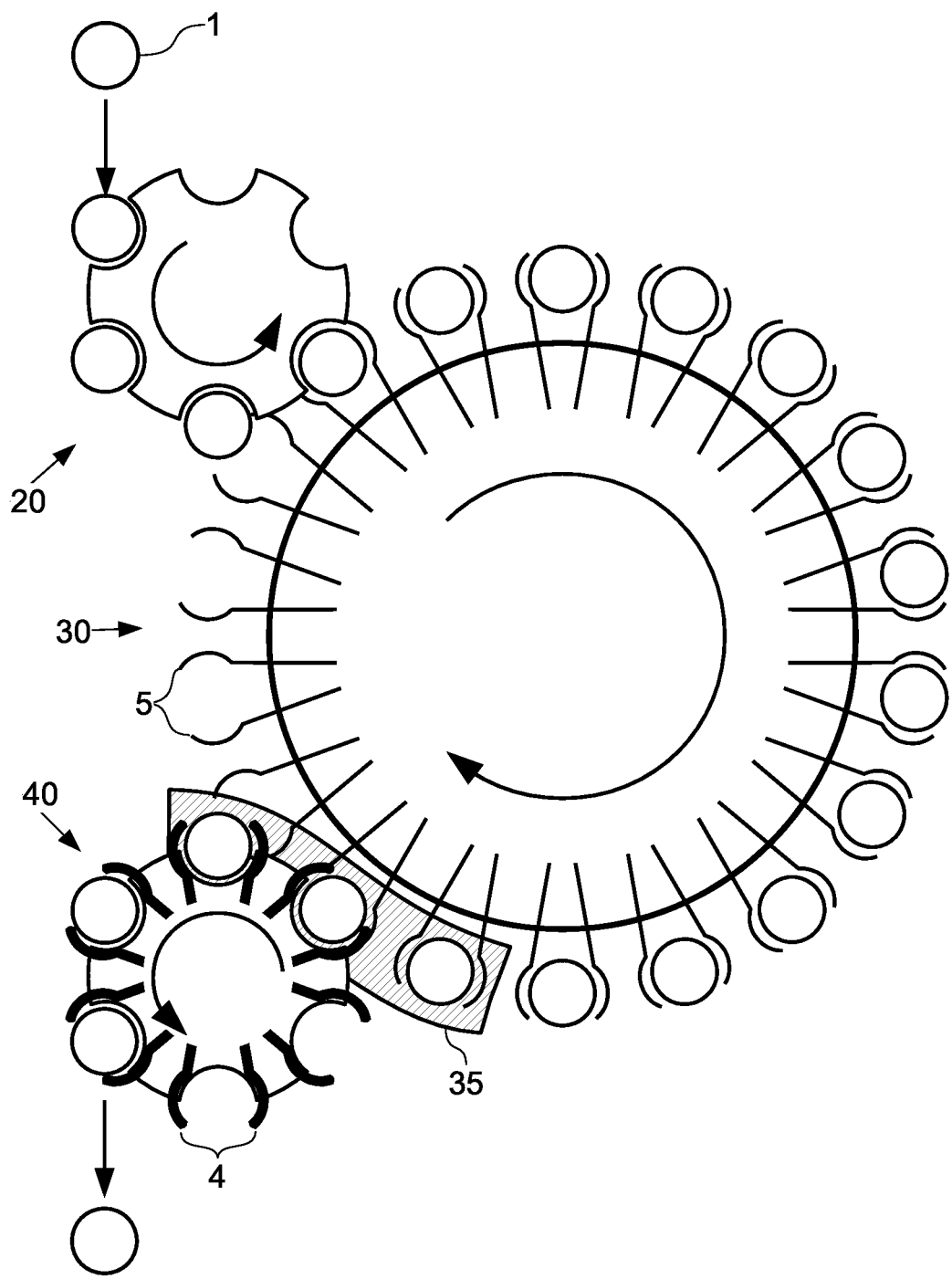
FIG. 3 shows a top view of a transport unit with an inspection device according to the present disclosure.

FIG. 3 shows schematically a top view of a transport unit with an inspection apparatus according to the present disclosure. The containers 1, arriving from above in the drawing, are introduced in a processing carousel 30 by means of an infeed star wheel 20, and from this processing carousel 30 they can be transferred by means of a discharge star wheel 40 so that further processing can take place. The processing carousel 30 may e.g. be a labeling device. The excitation can take place e.g. with the aid of a thrust plate 35 in the transition area between the processing carousel 30 and the discharge star wheel 40. The sensors (not shown) and the associated application devices 4 are arranged in the discharge star wheel 40. The arrows illustrate the direction of rotation of the respective components.

According to a preferred embodiment, the excitation device and the sensor application device are separated in space. As explained above, the excitation may take place e.g. in the processing carousel 30 or in the transition area between the processing carousel 30 and the discharge star wheel 40, signal detection being then executed in the discharge star wheel 40. Excitation may take place in any suitable way. For example, thrust plates 35 for the containers may be configured (e.g. fluted) such that the mere movement of the containers relative to the thrust plates will cause such excitation. Alternatively, vibration elements may be provided, which ensure an active excitation of the containers. For example, thrust plates 35, on which the containers are transported in an upright position, may be caused to vibrate vertically, which vibration will then be transmitted to the containers.

The transport unit shown in FIG. 3 may use any suitable holding device for the containers and may be combined with each of the above explained embodiments. In particular, the clamps 5 may also be replaced by the centering elements (centering bells) and bottle tables (rotary tables) outlined in FIG. 2. The containers may here be preloaded relative to the rotary tables by the centering bells. The embodiments of the excitation device (vibration device and rotation device) described in connection with FIG. 1 as well as FIG. 2 can both be used instead of the thrust plate 35 and can be arranged in the processing carousel as well as in the discharge star wheel.

What is claimed is:

1. An apparatus for inspecting filled containers for foreign bodies while the container to be inspected is fixed in a transport unit by means of a holding element and transported along a predetermined trajectory, comprising:
    an excitation device configured for mechanically exciting the container so that foreign bodies that may be present in the container will be caused to move,
    a sensor,
    an application device configured for applying the sensor to the container,
    the sensor being configured for detecting, when applied, acoustic signals of the foreign bodies that have been caused to move through mechanical excitation, and
    the application device configured for bringing the sensor into contact with the container only after an end of the mechanical excitation.

2. The apparatus according to claim 1, wherein the application device is arranged downstream of the excitation device, when seen in the direction of transport.

3. The apparatus according to claim 1, wherein the transport unit comprises a processing carousel and a downstream transfer star wheel, the excitation device being arranged in the processing carousel or in a transition area between the processing carousel and the transfer star wheel, and the application device being arranged in the transfer star wheel.

4. The apparatus according to claim 1, wherein the excitation device is configured for causing the container to at least one of rotate or vibrate.

5. The apparatus according to claim 1, wherein the sensor includes a piezoelectric element and is configured for detecting acoustic signals originating from foreign bodies impacting an inner wall of the container.

6. The apparatus according to claim 1, wherein the sensor, when applied, is moved along the predetermined trajectory.

7. The apparatus according to claim 1, wherein the transport unit comprises a clamp star wheel and the sensor is integrated in a clamp of the clamp star wheel.

8. The apparatus according to claim 1, wherein the application device comprises one of a control cam, a lifting cam, a motor, a linear motor and a servomotor for controlling the movement of the sensor.

9. The apparatus according to claim 1, further comprising an analysis unit configured for analyzing the acoustic signal detected by the sensor in at least one of the time or the frequency domain and for deciding, on the basis of the analysis, if a foreign body is present in the container.

10. The apparatus according to claim 1, wherein the excitation device comprises a motor that is capable of causing the container to rotate.

11. The apparatus according to claim 10, wherein the rotation of the container is about the longitudinal axis thereof.

12. The apparatus according to claim 1, wherein the application device is configured for bringing the sensor into contact with an outer wall of the container.

13. The apparatus according to claim 12, wherein the outer wall is a side wall.

14. A method for inspecting filled containers for foreign bodies while the container to be inspected is fixed in a transport unit by means of a holding element and transported along a predetermined trajectory, comprising:
   mechanically exciting a container so that foreign bodies that may be contained therein will be caused to move,
   applying a sensor to the container,
   detecting, by means of the sensor applied, acoustic signals originating from the foreign bodies that have been caused to move through the mechanical excitation, and
   applying the sensor to the container only after the end of the mechanical excitation.

15. An apparatus for inspecting filled containers for foreign bodies while the container to be inspected is fixed in a transport unit by means of a holding element and transported along a predetermined trajectory, comprising
   an excitation device configured for mechanically exciting the container so that foreign bodies that may be present in the container will be caused to move, the excitation device including a vibration unit preloaded relative to the container via an elastic element,
   a sensor,
   an application device configured for applying the sensor to the container,
   the sensor being configured for detecting, when applied, acoustic signals of the foreign bodies that have been caused to move through mechanical excitation, and
   the excitation device adapted to be brought into contact with the container independently of the holding element.

16. The apparatus according to claim 15, wherein the elastic element is a spring.

17. A method for inspecting filled containers for foreign bodies while the container to be inspected is fixed in a transport unit by means of a holding element and transported along a predetermined trajectory, comprising:
   mechanically exciting a container by means of an excitation device so that foreign bodies that may be contained therein will be caused to move, in mechanically exciting the container, exciting the container by an excitation device configured for mechanically exciting the container so that foreign bodies that may be present in the container will be caused to move, the excitation device including a vibration unit preloaded relative to the container via an elastic element,
   applying a sensor to the container,
   detecting, by means of the sensor applied, acoustic signals originating from the foreign bodies that have been caused to move through mechanical excitation, and
   bringing the excitation device into contact with the container independently of the holding element.

18. The method according to claim 17, wherein in mechanically exciting the container, the elastic element is a spring.

* * * * *